United States Patent [19]

Hrebeniuk

[11] Patent Number: Plant 7,293

[45] Date of Patent: Aug. 7, 1990

[54] DISTINCT VARIETY OF POINSETTIA NAMED H-110-18 RED

[76] Inventor: Alexander Hrebeniuk, R.D. #1, Box 118, Sugar Run, Pa. 18846

[21] Appl. No.: 339,159

[22] Filed: Apr. 17, 1989

[51] Int. Cl.[5] ..... A01H 5/00
[52] U.S. Cl. ..... Plt./86
[58] Field of Search ..... Plt./86

*Primary Examiner*—Howard J. Locker

*Attorney, Agent, or Firm*—Webb, Burden, Ziesenheim & Webb

[57] ABSTRACT

A Poinsettia plant named H-110-18 Red particularly characterized by the combined characteristics of double form, dark green leaves, dark red non-fading bracts, eight week response time, long lasting centers with continuing development of bracts after centers have dropped. Plants are long lasting under home ambient temperature, and have upright and compact growth habit with free branching.

1 Drawing Sheet

BACKGROUND OF THE NEW PLANT

The present invention comprises a new and distinct cultivar of *Euphorbia pulcherrima* known by the varietal name H 110-18 Red. The new cultivar is a sport from H-365 Red (U.S. Plant Pat. No. 6,491).

The new cultivar was discovered in June of 1987 in Sugar Run, Pa.; was first asexually reproduced by cuttings shortly thereafter in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this Poinsettia as new and distinct:

1. Eight week response time under black cloth.
2. Six to seven breaks after pinch, bloom type flat and fluffy.
3. May be grown single stem or pinch.
4. Top leaves dark green.
5. Mature leaves lighter.
6. Petioles very dark red on top, and lighter red on bottom.
7. Veins in leaves on top dark green and shiny, on bottom veins red to pinkish.
8. Stem on bottom green and on top greenish-red.
9. Bracts are dark red and do not fade.
10. The centers of the bloom are long lasting.
11. The red bracts continue to develop after the centers have dropped.
12. Blooms have on a pinch plant double layers of bracts which are flat and slightly fluffy.
13. Twenty (20) to twenty-eight (28) bracts have been counted on a fully developed pinch plant.
14. The largest bloom size measured on a single stem have been 13–14 inches in diameter.
15. Bracts range in size on a pinch plant from three (3) cm. to five (5) cm. wide to five (5) cm. long, to ten (10) cm. wide and fifteen (15) cm. long.
16. The new cultivar shows the bracts are fully developed by the end of November.
17. Responds very well to the growth regulator cycocel.
18. Plants keep up from November to spring under ambient home temperature.

19. Plants ship well.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The plant history was taken on eight week plants. The color readings were determined under natural daylight at Sugar Run, Pa. Color references are primarily to the R.H.S. Colour Chart of The Royal Horticultural Society of London.

The plant:

*Form.*—Double.

*Growth habit.*—Medium height, upright and compact, very freely branching after pinched. Grows and flowers well under cool conditions.

*Rooting.*—Fast and well.

*Blooming season.*—Eight weeks.

*Blooming habit.*—Medium to large, develop in double layer, with the color resistant to fade.

Foliage:

*Size.*—From 6 cm. wide and 10 cm. long, to 9 cm. wide and 14 cm. long.

*Quantity.*—12 to 14 leaves per flowering stem.

*Color.*—New foliage — Upper side, Green Group 139 A. Under side, Green Group 139 B. Old foliage — Upper side, Green Group 137 A. Under side, Green Group 137 B. Leaf petiole — Upper side, Red-Purple Group 59 A. Under side, Red-Purple Group 59 B.

*Shape.*—Oak to heart shaped.

*Texture.*—Upper side velvety. Under side smooth between veins.

*Edge of margin.*—Varied and slightly wavy to pointed.

*Disease resistance.*—Resistant to Botrytis.

Flower:

*Borne.*—In a compound corymb.

*Quantity.*—No more than 20 per stem, each flower having a nectary.

*Color.*—Green Group 139 D, Orange Group 169 D, and Red Group 57 B.

Bracts:

*Size.*—From 3 cm. wide to 5 cm. long, to 10 cm. wide and 15 cm. long.

*Color.*—Upper side, Red Group 53 B. Under side, Red Group 53 C.

Reproductive organs: Typically for Poinsettia cultivars.

I claim:

1. A new and distinct variety of Poinsettia plant as herein shown and described, particularly characterized by its double form, dark green leaves, dark red non-fading bracts, eight week response time, long lasting centers with continuing development of bracts after centers have dropped, long lasting under home ambient temperature, upright and compact growth habit with free branching.

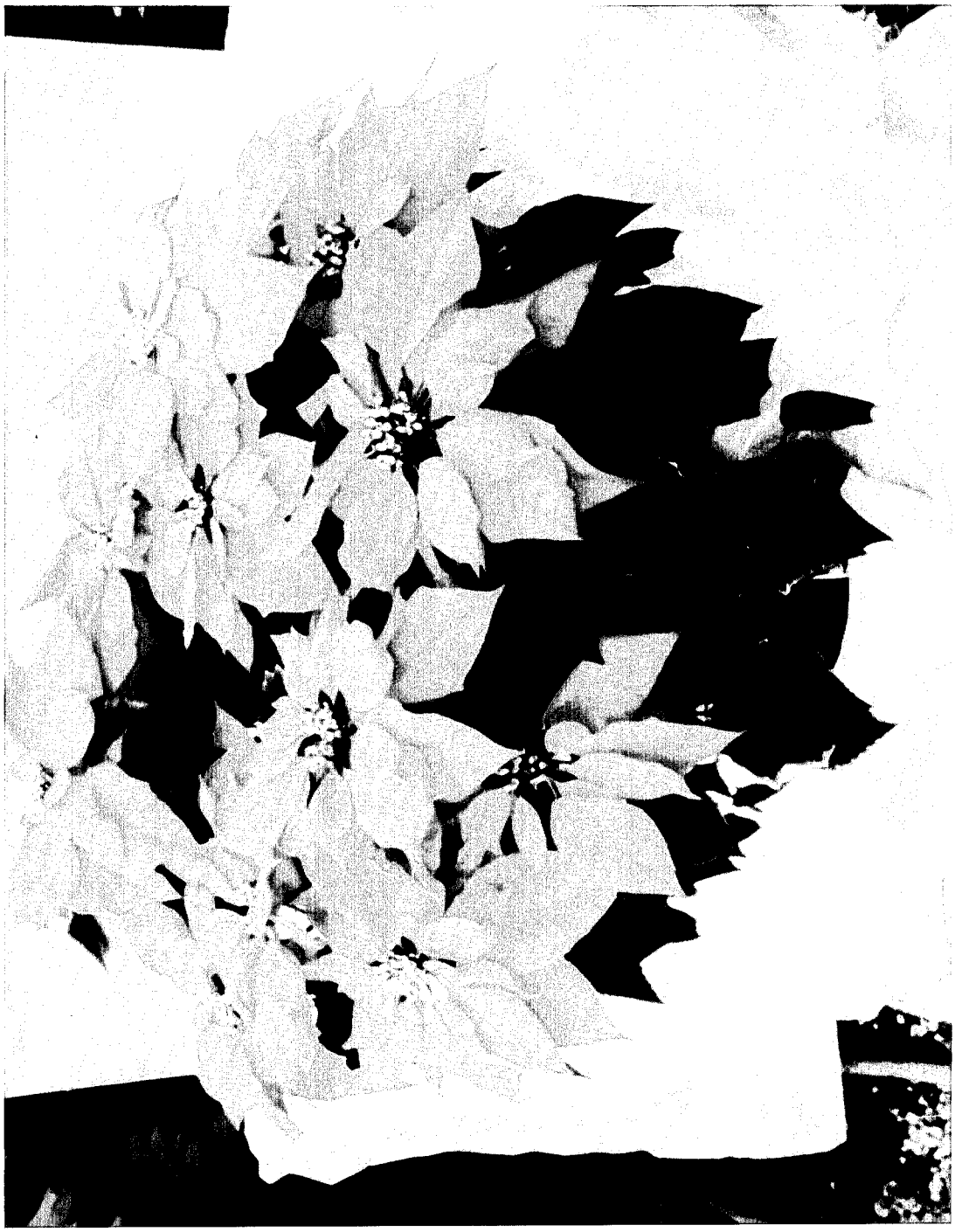

* * * * *